US010928380B2

(12) United States Patent
Shortt et al.

(10) Patent No.: US 10,928,380 B2
(45) Date of Patent: Feb. 23, 2021

(54) DIGESTIVE PROFILING SYSTEM

(71) Applicant: FoodMarble Digestive Health Ltd., Dublin (IE)

(72) Inventors: Aonghus Shortt, Dublin (IE); Matthew Lynch, Dublin (IE); Peter Harte, Louth (IE); Lisa Ruttledge, Kildare (IE); Patrick Dennis, Dublin (IE)

(73) Assignee: FOODMARBLE DIGESTIVE HEALTH LTD., Dublin (IE)

( * ) Notice: Subject to any disclaimer, the term of this patent is extended or adjusted under 35 U.S.C. 154(b) by 129 days.

(21) Appl. No.: 16/301,140

(22) PCT Filed: May 12, 2017

(86) PCT No.: PCT/EP2017/061532
§ 371 (c)(1),
(2) Date: Nov. 13, 2018

(87) PCT Pub. No.: WO2017/194774
PCT Pub. Date: Nov. 16, 2017

(65) Prior Publication Data
US 2019/0178868 A1  Jun. 13, 2019

(30) Foreign Application Priority Data

May 12, 2016 (GB) ..................... 1608365

(51) Int. Cl.
*G01N 33/497* (2006.01)
*A61B 5/00* (2006.01)
*A61B 5/083* (2006.01)

(52) U.S. Cl.
CPC ......... *G01N 33/497* (2013.01); *A61B 5/0002* (2013.01); *A61B 5/083* (2013.01); *A61B 5/48* (2013.01); *A61B 5/7475* (2013.01)

(58) Field of Classification Search
CPC .................................................. G01N 33/497
See application file for complete search history.

(56) References Cited

U.S. PATENT DOCUMENTS 9,299,238 B1 *  3/2016  Ahmad ............... A61B 5/4833
2012/0150056 A1  6/2012  Christman et al.
(Continued)

FOREIGN PATENT DOCUMENTS

EP        2821787 A1    1/2015
WO    2004/002307 A2    1/2004
(Continued)

OTHER PUBLICATIONS

Ong et al., "Manipulation of Dietary Short Chain Carbohydrates Alters the Pattern of Gas Production and Genesis of Symptoms in Irritable Bowel Syndrome: Dietary FODMAPs and IBS Symptoms," Journal of Gastroenterology and Hepatology, vol. 25, No. 8, Feb. 25, 2010.
(Continued)

*Primary Examiner* — Paul M. West
*Assistant Examiner* — Mark A Shabman
(74) *Attorney, Agent, or Firm* — BakerHostetler (57) ABSTRACT

A digestive profiling system comprises a breath analysis device comprising an inlet arranged to receive a breath sample from a user, a gas sensor arranged to generate a gas measurement of an amount of gas in the breath sample, and a first communication interface arranged to transmit a plurality of gas measurements generated by the gas sensor. The system further comprises a remote user interface device. The remote user interface device comprises a second communication interface arranged to receive the gas measurements generated by the gas sensor, a storage module arranged to store the received gas measurements, and a display arranged to display information to the user based on the stored gas
(Continued)

measurements. The remote user interface device is remote from the breath analysis device.

18 Claims, 9 Drawing Sheets

(56) References Cited

U.S. PATENT DOCUMENTS

| | | |
|---|---|---|
| 2012/0150153 A1 | 6/2012 | MacDonald |
| 2015/0250407 A1 | 9/2015 | Rigas |
| 2016/0370377 A1* | 12/2016 | Ahmad ............ A61B 5/150412 |
| 2017/0122931 A1* | 5/2017 | Carnahan ............. G01N 33/497 |

FOREIGN PATENT DOCUMENTS

| | | | |
|---|---|---|---|
| WO | 2011/104567 A1 | 9/2011 | |
| WO | WO-2011117572 A1 * | 9/2011 | ........... G01N 33/497 |

OTHER PUBLICATIONS

Cann et al., "Irritable Bowel Syndrome: Relationship of Disorders in the Transit of a Single Solid Meal to Symptom Patterns," Gut, vol. 24, No. 5, pp. 405-411, May 1983.

* cited by examiner

DIGESTIVE PROFILING SYSTEM

TECHNICAL FIELD

This disclosure relates to systems and methods for profiling the digestive system of a user.

BACKGROUND

Digestive conditions, such as irritable bowel syndrome (IBS), can be highly disruptive to the lives of people with these conditions. For example, the symptoms of IBS can include abdominal pain, bloating, diarrhoea and constipation. IBS affects about one in eight people worldwide, and, for the majority of people with IBS, existing medications are largely ineffective or have quite severe side-effects. Thus, there is a need to provide a solution for alleviating IBS sufferers from their symptoms.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

According to an aspect of the disclosure there is provided a digestive profiling system comprising: a breath analysis device comprising: an inlet arranged to receive a breath sample from a user; at least one gas sensor arranged to generate a gas measurement of an amount of gas in the breath sample; and a first communication interface arranged to transmit a plurality of gas measurements generated by the gas sensor; wherein the system further comprises a remote user interface device, the remote user interface device comprising: a second communication interface arranged to receive the gas measurements generated by the gas sensor; a storage module arranged to store the received gas measurements; and a display arranged to display information to the user based on the stored gas measurements; wherein the remote user interface device is remote from the breath analysis device.

According to an aspect of the disclosure there is provided a breath analysis device comprising: an inlet arranged to receive a breath sample from a user; at least one gas sensor arranged to generate a gas measurement of an amount of gas in the breath sample; and a communication interface arranged to transmit a plurality of gas measurements generated by the gas sensor to a remote user interface device.

According to an aspect of the disclosure there is provided a remote user interface device comprising: a communication interface arranged to receive gas measurements generated by at least one gas sensor of a breath analysis device; a storage module arranged to store the received gas measurements; and a display arranged to display information to the user based on the stored gas measurements; wherein the remote user interface device is remote from the breath analysis device.

According to an aspect of the disclosure there is provided a method of generating a digestive profile for a user, the method comprising: receiving a breath sample from the user through an inlet of a breath analysing device; generating a gas measurement of an amount of gas in the breath sample using at least one gas sensor at the breath analysing device; transmitting a plurality gas measurements generated by the gas sensor from a first communication interface at the breath analysing device; receiving the plurality of gas measurements at a second communication interface at a remote user interface device; storing the received gas measurements at the remote user interface device; and displaying the stored gas measurements at the remote user interface device.

According to an aspect of the disclosure there is provided a method of generating a digestive profile for a user, the method comprising: receiving a breath sample from the user through an inlet of a breath analysing device; generating a gas measurements of an amount of gas in the breath sample using at least one gas sensor at the breath analysing device; and transmitting a plurality gas measurements generated by the gas sensor from a first communication interface at the breath analysing device.

According to an aspect of the disclosure there is provided a method of generating a digestive profile for a user, the method comprising: receiving a plurality of gas measurements, generated by at least one gas sensor at a breath analysis device, at a communication interface at a remote user interface device; storing the received gas measurements at the remote user interface device; and displaying the stored gas measurements at the remote user interface device.

According to an aspect of the disclosure there is provided a computer program comprising code portions which when loaded and run on a computer cause the computer to execute a method as described herein.

BRIEF DESCRIPTION OF THE DRAWINGS

Embodiments of the invention will be described, by way of example, with reference to the following drawings, in which.

DETAILED DESCRIPTION

Figure 1:
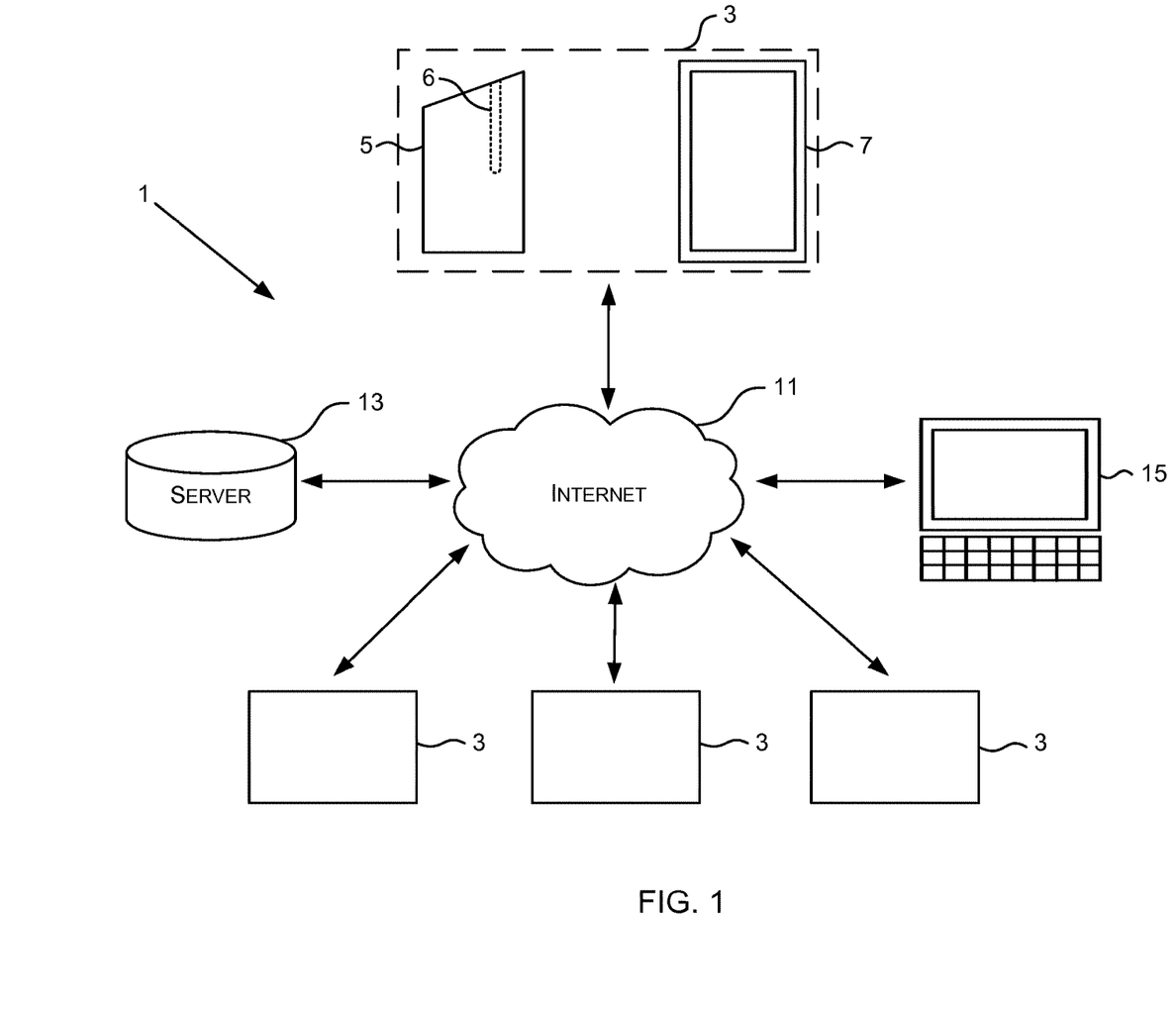
FIG. 1 schematically shows the basic general architecture of a system for generating a digestive profile of a user.

FIG. 1 schematically shows the basic general architecture which can be used in a digestive profiling system. The system 1 comprises a user-side system 3 comprising a breath analysis device 5 and a remote user interface device 7. The breath analysis device 5 comprises an inlet 6 into which a user may provide a sample of their breath.

Figure 2:
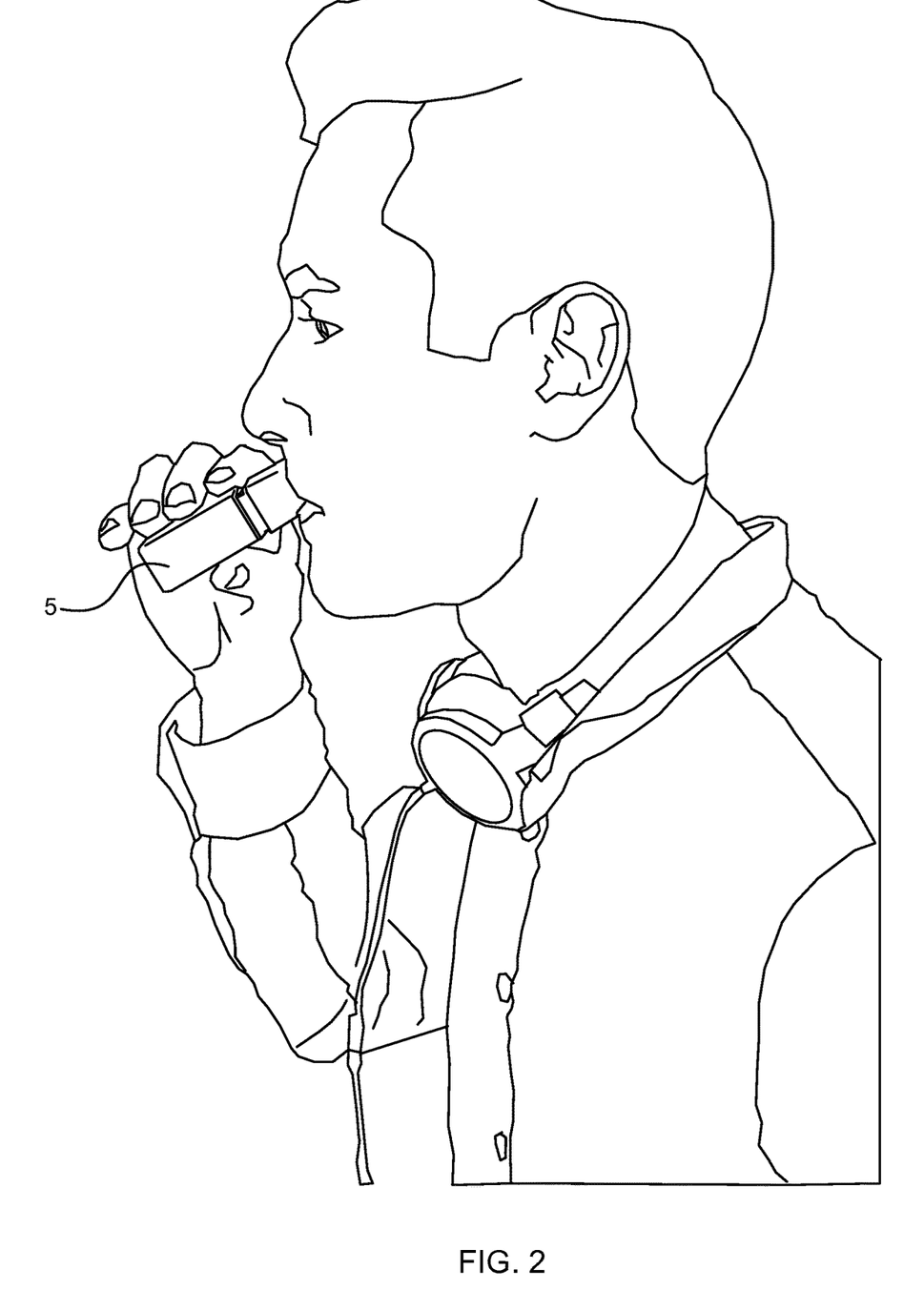
FIG. 2 schematically shows an illustration of a user providing a breath sample to a breath analyser.

FIG. 2 shows an illustration of a user providing a sample of their breath, or in other words a breath sample, to the breath analysis device 5. For the user to provide a breath sample, the user inhales air from the surrounding environment. Then, the user positions their mouth over the inlet 6 provided in the top of the breath analyser 5 (although the inlet may be provided at any suitable location on the analyser 5) and exhales at least a portion of their breath though the inlet 6. The breath analyser 5 measures the amount of a gas in the breath sample in order to obtain an indication of the state of the user's digestive system.

Gases emitted in a user's breath can be indicative of the current condition of that user's digestive system. For instance, a high concentration of hydrogen in a user's breath may indicate that the current condition of that user's digestive system is poor. On the other hand, a low concentration of hydrogen in a user's breath may indicate that the current condition of that user's digestive system is good.

In the following examples, the breath analyser 5 is arranged to measure the concentration of hydrogen in the user's breath. This may be particularly useful in analysing the condition of the user's digestive system, where the user is an IBS sufferer. For instance, a high concentration of hydrogen in a user's breath after consuming a food sample may indicate that the user's digestive system reacts negatively to that food sample.

The following examples focus on IBS and the measurement of the concentration of hydrogen in a user's breath. However, it will be appreciated that the system may measure quantities of other gases in a user's breath. This may be useful for the purposes of monitoring the condition of a user's digestive system generally, as well as for specific digestive conditions.

Referring to FIG. 1, the user interface device 7 is remote from the breath analysis device 5 so that the user interface device 7 is separate from and can be moved independently of the breath analysis device 5. In the following examples, the user interface device 7 comprises a handheld smartphone (or tablet), which is a mobile telephone that is web-enabled by including an embedded browser or "app" or similar. The smartphone 7 comprises a display screen, a user interface, a processor and a memory, as well as other features that will be described in greater detail below.

The smartphone 7 and the breath analysis device 5 are communicatively connected with one another via communications interfaces. In this example, the smartphone 7 and the breath analysis device 5 are arranged to communicate with one another via Bluetooth®. However, it will be appreciated that any other wireless communication protocol could be used instead.

As explained above, the breath analyser 5 measures the concentration of hydrogen in a user's breath sample. These measurements are communicated to the smartphone 7 and displayed to the user via the display screen. This provides the user with convenient access to gas measurements, which can allow the user to monitor their digestive profile more easily.

The remote nature of the user interface device 7 may allow the user to review their gas measurements in detail at any time and location. For instance, the user may wish to carefully analyse their gas measurements at a convenient moment and at a location that is not in-situ with the breath analysis device 5 itself. This may allow the user to draw more insightful conclusions from the gas measurements and to make better considered lifestyle decisions. This may help to alleviate their symptoms.

The system 1 may also comprise a plurality of other user-side systems 3 each comprising a respective breath analyser 5 and smartphone 7. Each of the user-side systems 3 may be connected to a server 13, via the Internet 11.

Data from the user-side systems 3 can be uploaded to the server 13. In this way, the system is able to store large amounts of data from a large number of users. The system 1 may also include an administrator device 15 which can be used by a user's doctor/clinician to access that particular user's gas measurements. This avoids the need for users to commit to regular visits to the doctor.

Figure 3:
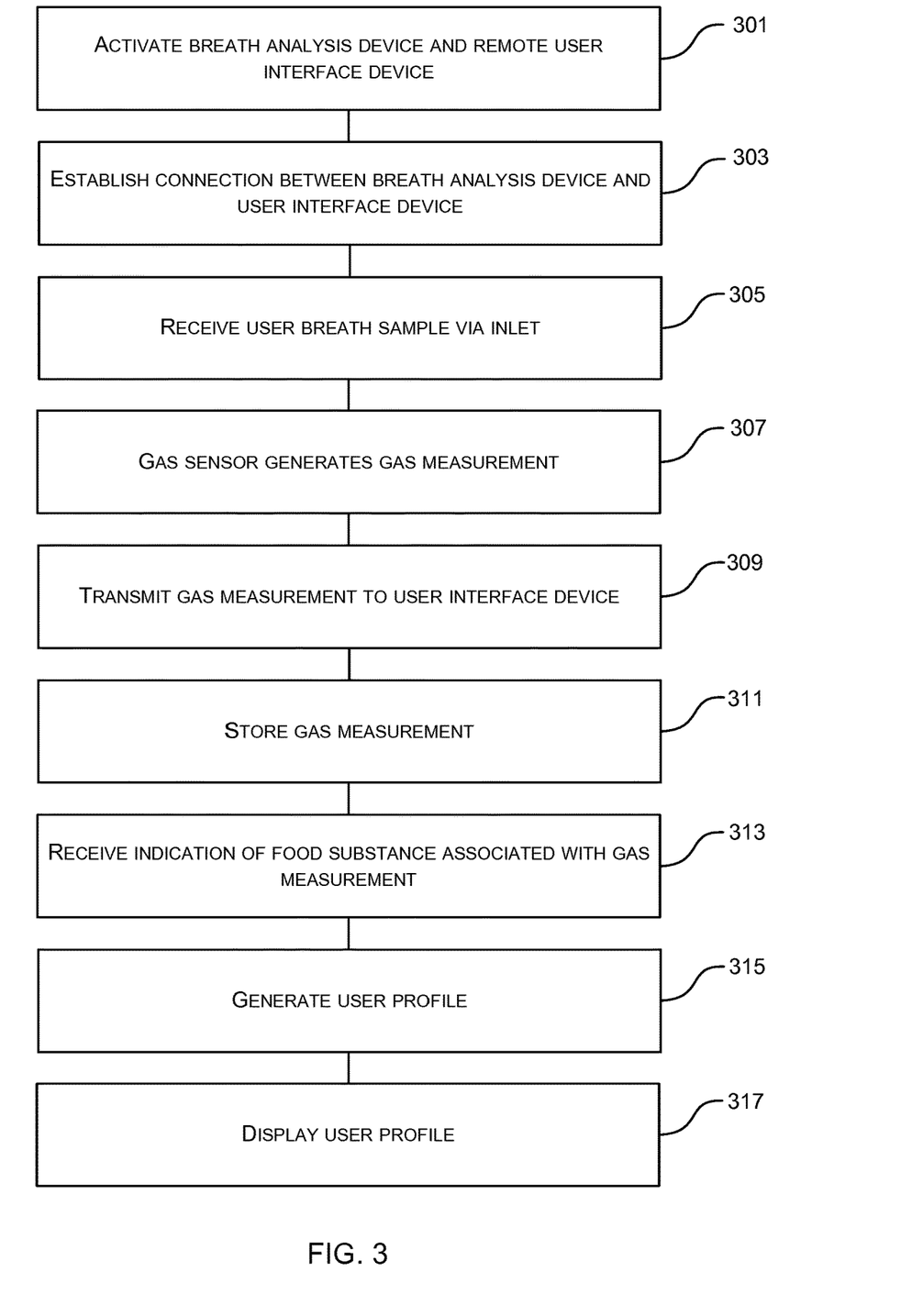
FIG. 3 shows a flow chart illustrating a method of generating a profile of a user's digestive system.

Referring to FIG. 3, in step 301 the breath analysis device 5 and the remote user interface device 7 are activated. In order to activate the breath analysis device 5, the user rotates a head portion of the device 5 relative to a base portion. This engages a switch which activates the breath analysis device 5. In another example, a button is provided for activating the device 5.

In step 303 a Bluetooth® connection is established between a first communication interface 17 of the breath analysis device 5 and a second communication interface 19 of the user interface device 7. This may involve the breath analysis device 5 being 'paired' with the user interface device 7.

After the breath analysis device 5 and the user interface device 7 are paired, the user may initiate an "app" at the user interface device 7. The app is used by the user for interacting with the system 1, for instance via a touch screen display 9. It would be possible for the user to initiate the app before pairing the breath analysis device 5 and the user interface device 7.

In step 305 the user provides a breath sample to the breath analysis device 5 by breathing into the inlet 6. This causes the user's breath to pass by a gas sensor 21 in the breath analysis device 5. In this example, the gas sensor 21 is a hydrogen sensor 21 for measuring the concentration of hydrogen in a breath sample. It is envisaged that the breath analysis device 5 may include or use a plurality of gas sensors. In one example, each one of a plurality of sensors could be used to measure other gases in addition to or instead of hydrogen, such as methane, in a similar manner as described herein.

Before the user provides a breath sample to the inlet 6, the voltage drop across the hydrogen sensor 21 is measured by a microcontroller unit (MCU). This voltage drop is converted to an ambient resistance value ($R_0$) which is indicative of the concentration of hydrogen in the surrounding atmosphere. When the user provides a breath sample, the minimum voltage drop across the hydrogen sensor 21 can be converted to the minimum sensor resistance ($R_{min}$) generated when exposed to the user's breath.

In step 307 the values of $R_{min}$ and $R_0$ are used to generate an accurate measurement of the concentration of hydrogen in the user's breath. In order to do this the MCU or the user interface device calculates a ratio of $R_{min}/R_0$ and the difference $R_0-R_{min}$, and references these against a two-parameter calibration curve for the sensor 21 to determine the hydrogen concentration.

The process of generating the gas measurement may occur within an integrated sensor. Alternatively, this process and its associated calculations may occur at a processing module. The above method for generating gas measurements is provided for exemplary purposes, and it will be appreciated that other methods could be used.

Figure 4:
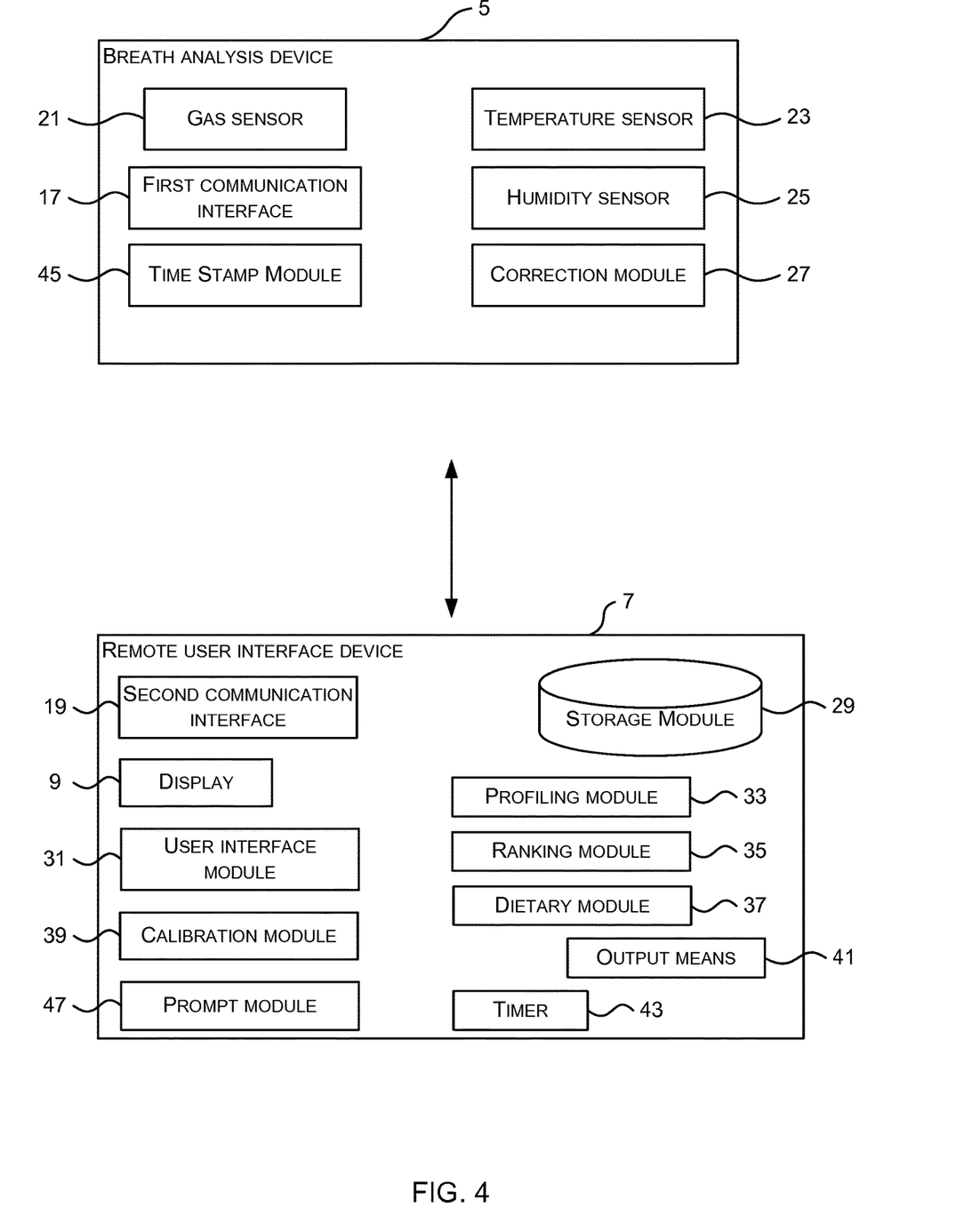
FIG. 4 schematically shows a part of the system shown in FIG. 1.

The breath analysis device 5 may also comprise a temperature sensor 23 and/or a humidity sensor 25, which are used to ensure that the gas measurements are accurate irrespective of the environment in which the measurements are taken. The temperature sensor 23 outputs a temperature measurement of the surrounding environment. The temperature measurement may be input into a correction module 27 at the breath analysis device 5, in order to adjust the gas measurement. In addition, the humidity sensor 25 may output a humidity measurement of the surrounding environment. The humidity measurement may be input into the correction module 27, in order to adjust the gas measurement.

In step 309 the first communication interface 17 receives the gas measurement of the hydrogen concentration in the user's breath and transmits the measurement, via Bluetooth®, to the second communication interface 19. In step 311, the gas measurement is stored at a store module 29 at the user interface device 7.

In step 313 the user interacts with a user interface module 31 at the user interface device 7 in order to identify a food substance that they consumed before providing the breath sample. The user interface module 31 may form part of the touch screen display 9. In addition, the user provides an indication that the identified food substance is associated with the gas measurement.

In step 315 the gas measurement is stored at the storage module 29. The gas measurement is stored in association with a food substance data item indicative of the respective food substance, which was consumed before providing the associated breath sample from which the gas measurement was generated.

In step 317 a profiling module 33 at the user interface device 7 generates a profile for the user based on the gas measurements and associated food substances. This profile may, for instance, take the form of a data file showing the gas measurements in association with a respective food substance. This profile may then be presented to the user via the display 9.

In general, gases emitted in a user's breath can be indicative of that user's reaction to a food substance that was consumed previously. For instance, a high concentration of hydrogen in a user's breath after consuming a particular type of food may indicate that the user's digestive system reacts negatively to that particular type of food.

In the digestive profiling system described above, the user identifies a food substance that has been consumed and associates that food substance with a corresponding gas measurement value. By collecting and storing a plurality of different gas measurements each in association with a respective identified food substance, the system can create a unique profile of that user's digestive system. This profile allows the user to manage their diet in order to alleviate symptoms of digestive issues that they may have.

Referring to FIGS. 3 and 4, the user interface device 7 includes a ranking module 35 that analyses each of the identified food substance data items stored in association with their respective gas measurements in the storage module 29. In one example, a particular food substance, for instance 'peach yogurt', may be stored in association with one or many gas measurements. If a greater number of gas measurements are stored in association with each food substance, this can allow the system to determine a more accurate indication of a user's suitability to a particular food substance. For example, the ranking module 35 may calculate an average gas measurement value for each food substance.

The ranking module 35 may determine a suitability score for each identified food substance based on its associated gas measurements. As an illustrative example, the ranking module 35 may associate a suitability score between 0 and 10 with each food substance. A suitability score of 0 may indicate that the food substance is not suitable for the user whatsoever. A suitability score of 5 may indicate that the food substance may be consumed by the user but is not advised. A suitability score of 10 may indicate that the food substance is very suitable for that user.

A 'high' suitability score may be derived from a low concentration of hydrogen and/or methane measured in a breath sample provided after consuming a particular food substance. A low' suitability score may be derived from a high concentration of hydrogen and/or methane measured in a breath sample provided after consuming another food substance. Thus, the ranking module 35 uses a negative correlation between the magnitude of the gas measurement and the suitability score. The terms 'high' and 'low' used herein refer to the positive and negative suitability of the food substance respectively, rather than the actual numerical score. It will be appreciated that any suitable scoring system could be used in place of the scoring process described above.

In one hypothetical example, a user has consumed a 'peach yogurt' a number of times and has recorded gas measurements of their breath samples afterwards. Here this hypothetical user's digestive system reacts well to 'peach yogurt', and thus the gas measurements associated with 'peach yogurt' will be low. This may result in a predicted high suitability score of '9' for 'peach yogurt' for that particular user.

The user interface device 7 may also comprise a dietary module 37 which is arranged to provide appropriate dietary information to a user based on the data in the storage module 29. In order to do this, the storage module 29 stores a plurality of dietary information data items each indicative of dietary information. For instance, the dietary information may include a particular diet, a particular meal, food type, or set of meals. Each piece of dietary information is stored in association with a related food substance data item, which is indicative of one of the food substances identified by the user.

The dietary module 37 interrogates the storage module 29 to identify a food substance data item associated with, for example, a high or a low suitability score. Then, the dietary module 37 identifies the dietary information data item associated with the identified food substance. The dietary information indicated by the data item can then be presented to the user via the display 9.

In the above hypothetical example, a piece of dietary information describing a meal suggestion may be associated with a food substance data item indicative of 'peach yogurt'. As explained above, the hypothetical user is well-suited to 'peach yogurt'. Thus, the dietary module 37 identifies the 'peach yogurt' data item by its high suitability score. Next, the associated meal suggestion is identified, which is then presented to the user.

In light of the above, the system allows a user to identify a suitable and personalised diet more easily. In choosing to follow the recommended diet a user may be able to alleviate the symptoms of a digestive condition that they may have.

Referring to FIG. 1, a plurality of different user-side systems 3 can provide the server 13 with gas measurements from different users. Each gas measurement is associated with a different food substance. The gas measurements and other associated data may be received by a third communication interface (not shown) at the server 13.

The server 13 may further comprise an analysis module (not shown) arranged to calculate an average suitability score for the food substances based on the received gas measurements. These average scores may then be presented to the users of the system. In this way the users may appreciate which foods are generally suitable and unsuitable. Thus, the users may be able to change their diet accordingly. This may help to alleviate digestive system condition symptoms.

The user interface device 7 may allow the user to select a food type to which they are well suited. The device 7 may then recommend a suitable meal which contains that food type. If the food type is not suitable for the user, the device may suggest an alternative food type that is suitable for the user.

Figure 5:
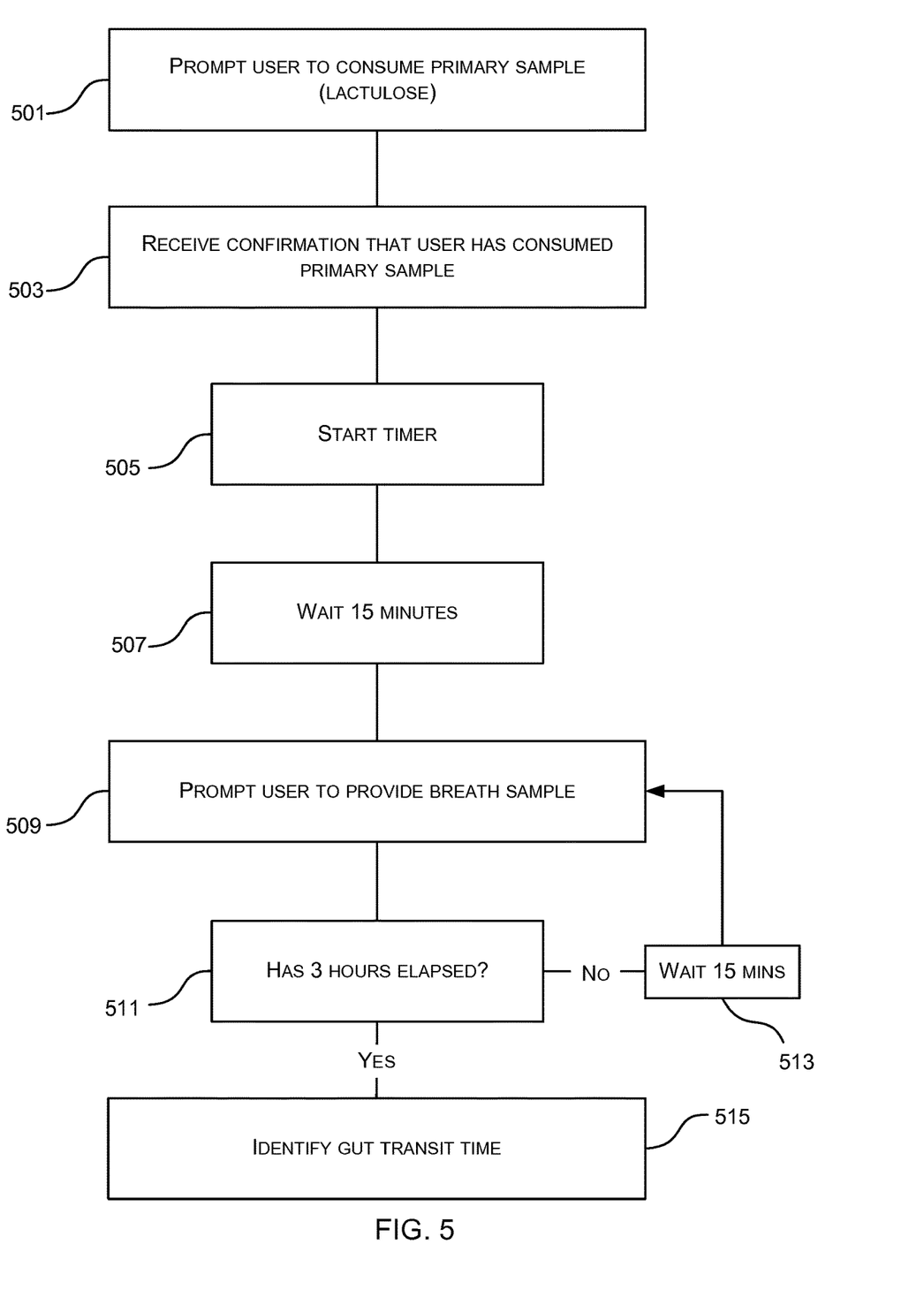
FIG. 5 shows a flow chart illustrating a first method for calibrating the system shown in FIGS. 1 and 4.

A first method for calibrating the digestive profiling system will now be described with reference to FIGS. 1, 4 and 5. In step 501 the user navigates through an app installed at the user interface device 7 to initiate an initial calibration procedure. This procedure may be initiated on first use of the app with the breath analysis device 5 in order to calibrate the system 1 to an individual user. Once the initial calibration procedure is initiated, a calibration module 39 prompts the user, via output means 41 to consume a primary food substance sample.

In this example, the primary sample comprises a sample of lactulose. Here the lactulose sample is provided to the user along with the breath analysis device 5. Before consuming the user is required to mix the sample with a specific quantity of water. The instructions for doing this may be presented to the user via the display 9 of the user interface device 7.

In this example, it is envisaged that the output means 41 comprises the display 9 and an audio output at the user interface device 7. However, the prompt may be delivered to a user via any appropriate output means.

In response to the prompt, the user consumes the lactulose in the manner requested. Then, in step 503, the user may provide an indication, via the user interface module 31, that they have consumed the lactulose sample. This may cause the calibration module 39 to activate a timer 43 in step 505.

In this example, the user is required to indicate when they have consumed the sample. This may allow the system to more accurately determine the elapsed time since the sample was consumed. In another example, the timer 43 is activated by the calibration module 39 in response to the initial prompt in step 501. Although this may provide a less accurate way of determining the elapsed time, it requires fewer-interactions between the user and the interface device 7.

In step 507 the calibration module 39 waits until a time interval (of, for instance, 15 minutes) has elapsed since the sample was consumed based on the time indicated by the timer 43. The time interval may be set by the user. Then in step 509, the calibration module 29 causes the output means 41 to prompt the user to provide a breath sample.

In response to the prompt, the user provides a breath sample in the manner described above. This causes a gas measurement to be generated. When the gas measurement is generated it is associated with a time stamp generated by a time stamp module 45 at the breath analysis device 5. Next the gas measurement and its associated time stamp are sent via the communication interfaces 17, 19 for storage at the storage module 29.

In step 511 the method checks to see if a maximum interval time, which in this example is 3 hours, has elapsed since the user consumed the primary sample. If not, the method waits another 15 minutes (step 513) before prompting the user to provide another breath sample in step 509. Steps 511, 513 and 509 are repeated until the 3 hours have elapsed since the user consumed the primary sample. During this period the gas measurements and their respective time stamps are stored at the storage module 29.

Once 3 hours have elapsed the method proceeds to step 515 in which the calibration module 39 identifies an estimate of the 'gut transit time' (GTT) for the user based on the gas measurements and time stamps. The GTT is indicative of the amount of time that a food sample takes to travel from someone's mouth to their colon.

In order to estimate the GTT, the calibration module 39 identifies the elapsed-time at which the peak hydrogen concentration was measured within the 3 hour time period. It has been found that the peak hydrogen measurement should not occur earlier than 15 minutes from consumption and should not occur later than 3 hours from consumption. Thus having 15 minute time intervals between prompts and a maximum time interval of 3 hours is a convenient way of obtaining an accurate estimate of the GTT.

In the above example lactulose is used as the primary sample in the initial calibration procedure, although it is envisaged that other substances could be used. Using lactulose is particularly advantageous because it should result in strong fermentation in the user's digestive system. This makes the peak hydrogen measurement easier to identify and therefore allows the GTT to be estimated more easily. Other possible substances that could be used as the primary sample substance include: glucose, lactose, fructose, sorbitol, inulin, raffinose, xylitol, mannitol and/or any carbohydrate. In addition, recorded gas measurements in association with the different substances from the calibration process can indicate the user's suitability to a variety of different foods, as described herein.

After the first method for calibrating the system has been completed, the first method may be repeated with different samples. For instance, glucose, lactose, fructose or sorbitol could be used.

Figure 6:
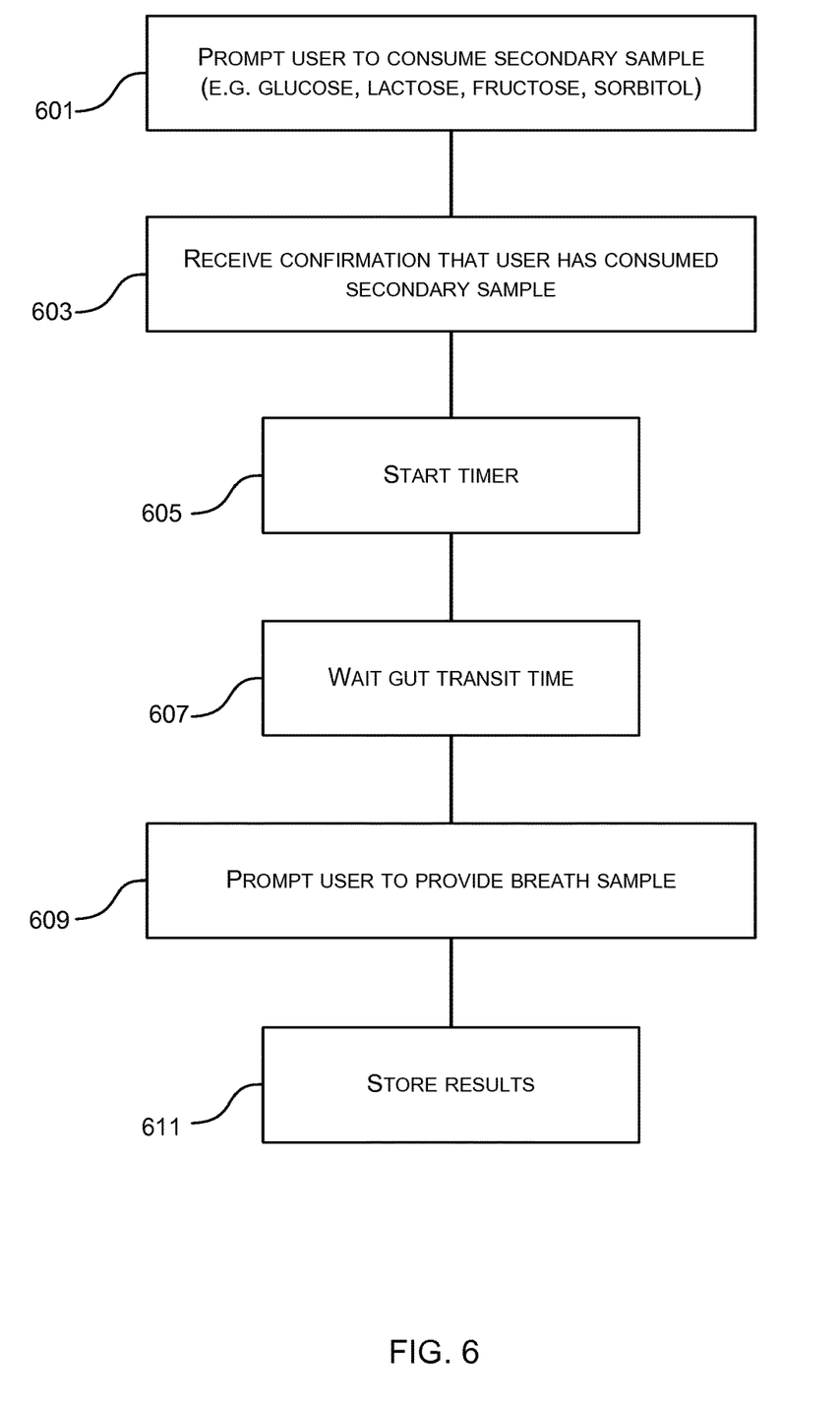
FIG. 6 shows a flow chart illustrating a second method for calibrating the system shown in FIGS. 1 and 4.

A second method for calibrating the digestive profiling system will now be described with reference to FIGS. 1, 4 and 6. In step 601 the user navigates through the app installed at the user interface device 7 to initiate a secondary calibration procedure. Once the secondary calibration procedure is initiated, a calibration module 39 prompts the user via output means 41 to consume a secondary food substance sample.

In the following example glucose is used as the secondary food substance for the secondary calibration procedure; however, other food substances could be used, such as lactulose, lactose, fructose, sorbitol, inulin, raffinose, xylitol, mannitol and/or any carbohydrate.

In response to the prompt, the user should consume the glucose in the manner requested. Then in step 603, the user may provide an indication, via the user interface module 31, that they have consumed the glucose. This may cause the calibration module 39 to activate a timer 43 in step 605.

As explained previously, the user is required to indicate when they have consumed the sample. This may allow the system to more accurately determine the elapsed time since the sample was consumed. In another example, the timer 33 is activated by the calibration module 39 in response to the initial prompt in step 601. Although this may provide a less accurate way of determining the elapsed time, it requires fewer-interactions between the user and the interface device 7.

In step 607 the calibration module 39 waits until a predetermined estimate of the user's gut transit time (or a predetermined time period, such as 15 minutes) has elapsed since the sample was consumed. The calibration module 39 monitors the elapsed time based on the time indicated by the timer 43. Preferably, the predetermined estimate of the user's gut transit time is equal to the GTT identified in step 515, as previously described.

In step 609, the calibration module 29 causes the output means 41 to prompt the user to provide a breath sample. In response to the prompt, the user provides a breath sample in the manner described above. This causes a gas measurement to be generated. When the gas measurement is generated it is associated with the time stamp generated by a time stamp module 45 at the breath analysis device 5. Then in step 611, the gas measurement and its associated time stamp are sent via the communication interfaces 17, 19 for storage at the storage module 29. Steps 605-611 may be repeated over a series of predetermined time intervals.

The secondary calibration procedure can be repeated using each one of glucose, lactose, fructose and sorbitol as the secondary food substance sample in separate repetitions of the procedure. These substances can be used to create an accurate picture of a user's digestive system. By analysing a user's response to just these four food substances, it is possible to assess that user's compatibility with a wide range of foods. It is envisaged that other substances such as lactulose, inulin, raffinose, xylitol, mannitol and/or any carbohydrate could be used as well. For instance, the gas measurement for each sample may be stored in association with the food substance sample as the identified food substance, as explained previously.

Based on the results from the calibration methods in steps 501-515 and steps 601-611, the ranking module 35 is able to generate a suitability score for each one of the samples: lactulose, glucose, lactose, fructose and sorbitol etc. These food substances can be associated with dietary information, such as a particular meal that has a high or low content of at least one of these food substances. Therefore, based on the suitability scores the ranking module 35 the system is able to recommend meals that may be particularly suitable or unsuitable for an individual user. The secondary calibration procedure may be conducted instead of or in addition to the primary calibration procedure.

Figure 7:
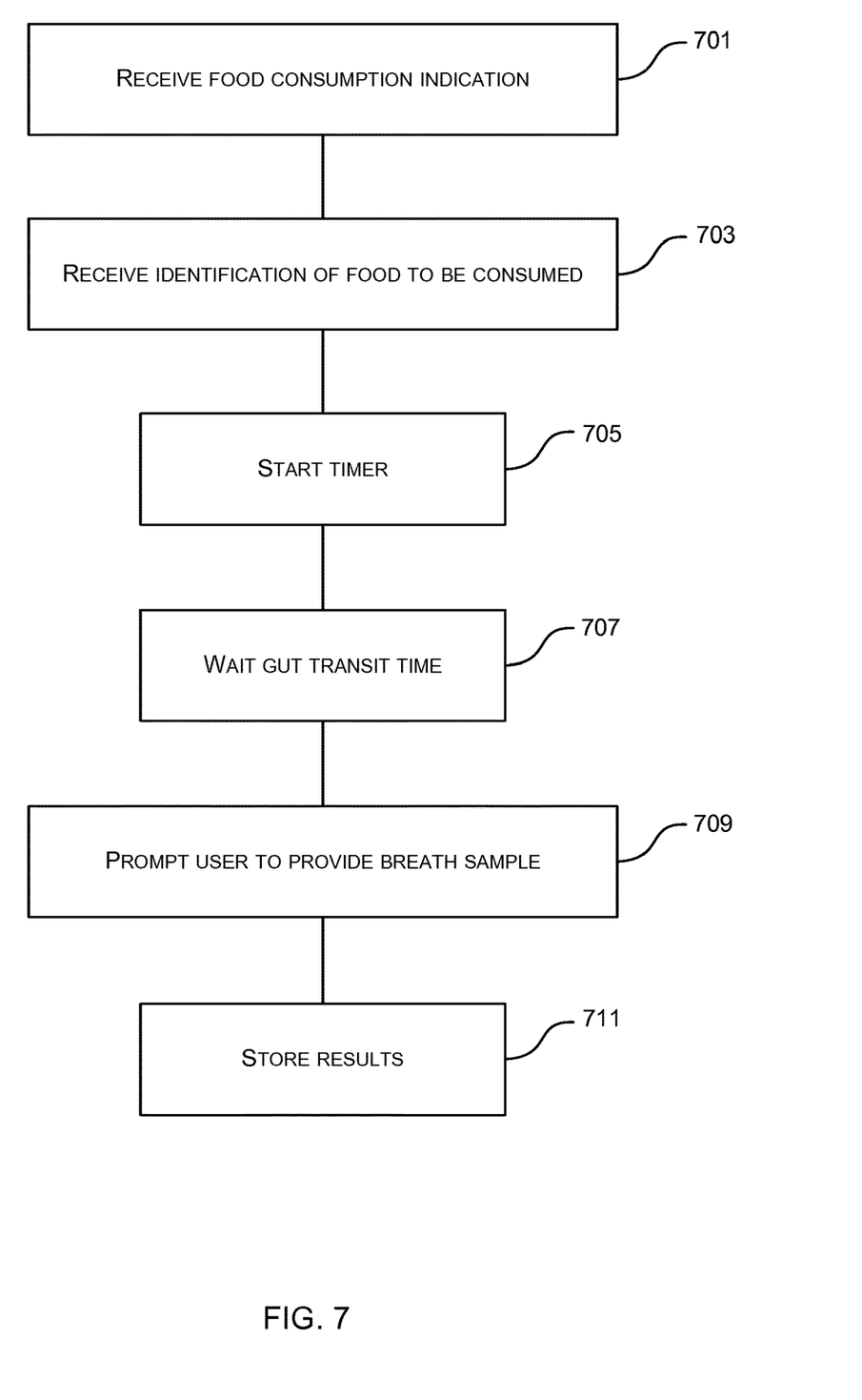
FIG. 7 shows a flow chart illustrating an extended method of generating a profile of a user's digestive system.

An extension of the method of generating a profile of a user's digestive system will now be described with reference to FIGS. 1, 4 and 7. In step 701 the user provides an indication that they are about to begin a food consumption session, or in other words a meal. This indication may be received by the user interacting with the user interface module 31, for instance via a touch screen display 9. The user may provide this indication using the app installed at the user interface device 7. In one example, the user takes a photograph of their meal using a camera and the app at the user interface device 7. This photograph may be stored at the storage module 29. This may be used to provide the user of a visual log of their eating habits.

In step 703 the user provides an identification of the food in the meal. In order to do this the user may interact with the user interface module 31 via the app to input a textual description of the meal. For example, the user may give a general description of the meal, such as 'burger and chips', along with a description of the food types in the meal, such as 'fried beef, bread and fried potatoes'. In another example, the user may identify the food types from a menu presented by the app.

In response to either step 701, step 703 or a further indication from the user, the timer 43 may be activated in step 705. Then a prompt module 47 waits until a predetermined estimate of the user's gut transit time has elapsed since the meal was consumed. The prompt module 47 monitors the elapsed time based on the time indicated by the timer 43. Preferably, the predetermined estimate of the user's gut transit time is equal to the GTT identified in step 515, as previously described. Then in step 709, the prompt module 29 causes the output means 41 to prompt the user to provide a breath sample.

In response to the prompt, the user provides a breath sample in the manner described above. This causes a gas measurement to be generated. When the gas measurement is generated it is associated with a time stamp generated by the time stamp module 45. Then in step 711, the gas measurement and its associated time stamp are sent via the communication interfaces 17, 19 for storage at the storage module 29.

In step 711 each gas measurement is stored in association with the identified food substance. This allows the user to create an on-going record of their diet in association with gas measurements that show how their digestive reacts to particular foods. This information can be used to create a more accurate profile of the user's digestive system as described above. It can also be used to recommend certain foods and diets to the user. This may help the user to alleviate symptoms of a digestive condition. In addition, it is envisaged that gas measurements can be stored independently and/or without being associated with a particular food substance.

Any of the methods described above may include the optional and additional step of taking a gas measurement from a breath sample before the user consumes a food sample. This allows the system to obtain a baseline reading to which subsequent readings may be compared. The system may prompt the user to provide this baseline reading in a similar fashion to that described above.

Figure 8:
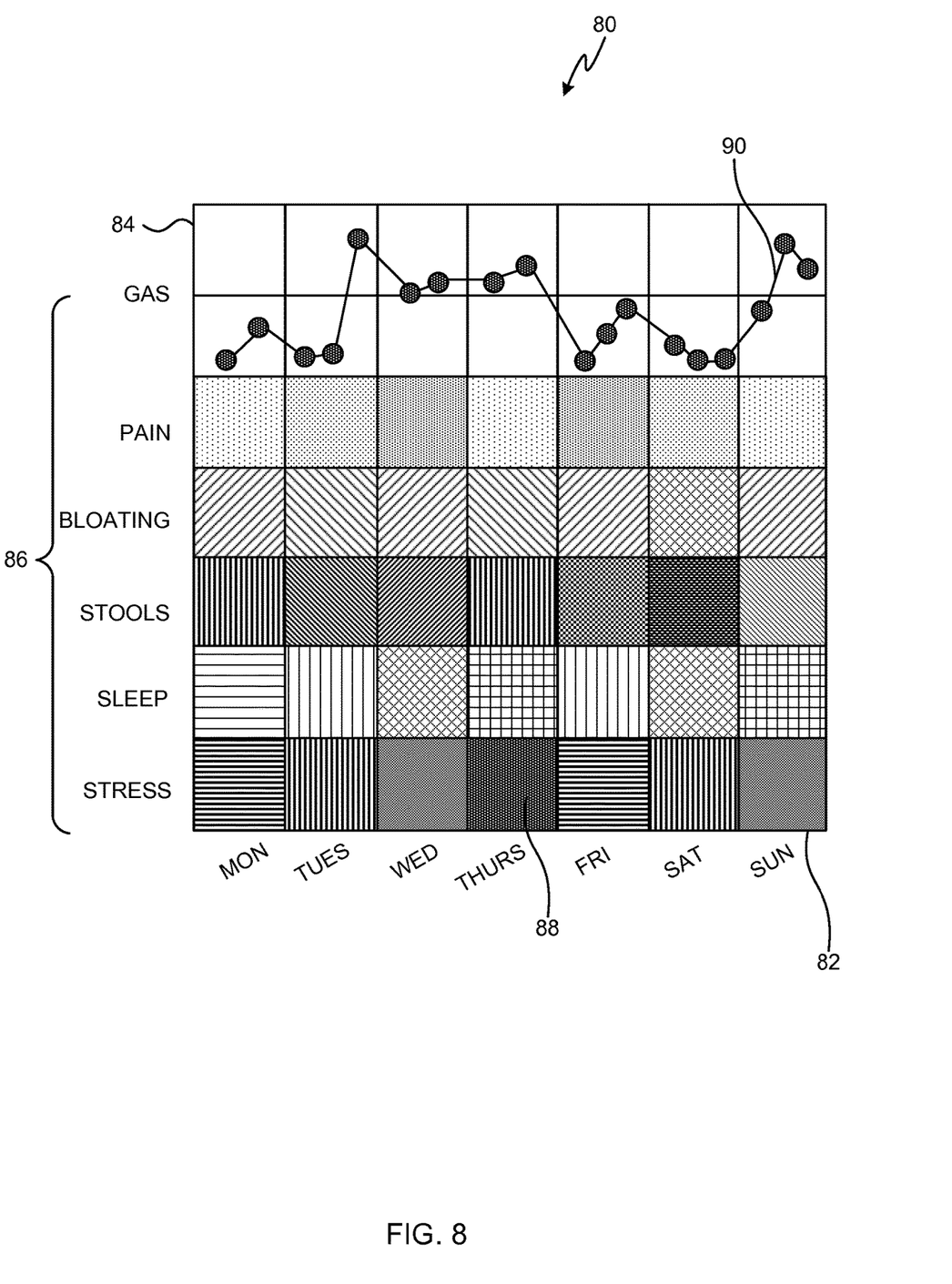
FIG. 8 shows an example of a user's digestive profile.

FIG. 8 shows an example of a chart 80 illustrating the user's digestive profile. In this case, the chart 80 may be described as a seven day review of the user's digestive profile. This graph may be generated from data stored in the storage module 29 of the user interface device 7. In other examples, the chart may present a 48 hour or one day review of the user's digestive profile.

A horizontal axis 82 of the chart 80 shows the user's profile in the time domain. In this example, the horizontal axis 82 shows days of a week in which the user recorded gas measurements. A vertical axis 84 of the chart 80 shows the different symptom characteristics (or digestive factors) 86, such as gas level, digestive pain, bloating, stool consistency, sleep quality and stress level. These symptom characteristics may be related to a user's digestive condition, such as IBS.

Every day the user may prompted to provide a rating based on each one of the symptom characteristics. For example, each day the prompt module 47 may prompt the user to rate their digestive pain, bloating, stool consistency, sleep quality and stress level on a scale of 0-10. These scores may be presented to the user via the shading shown in the grid.

In addition to the score, the graph 90 shows the level of the gas measurements recorded by the user throughout the week. A user may click on a point on the graph 90 to access information about the food associated with the gas measurement from which the point was generated. For example, in response the app may present the user with their photograph of the meal and corresponding text which were input before providing the corresponding breath sample.

The chart 80 provides a simple way of communicating the user's digestive profile, whilst minimising the amount of space required for the graph at the display 9 of the user interface device 7.

The user profile may be input into a predictive model which can output a measure of how likely the user is to experience negative symptoms. For example, if a user's gas readings are increasing as a day goes on, then based on this, the system can notify the user to avoid all low suitability foods that day. In another example, if a user's gas readings are considered low for a period of time, the system can notify the user that they may be able to manage a low suitability food that day.

Figure 9:
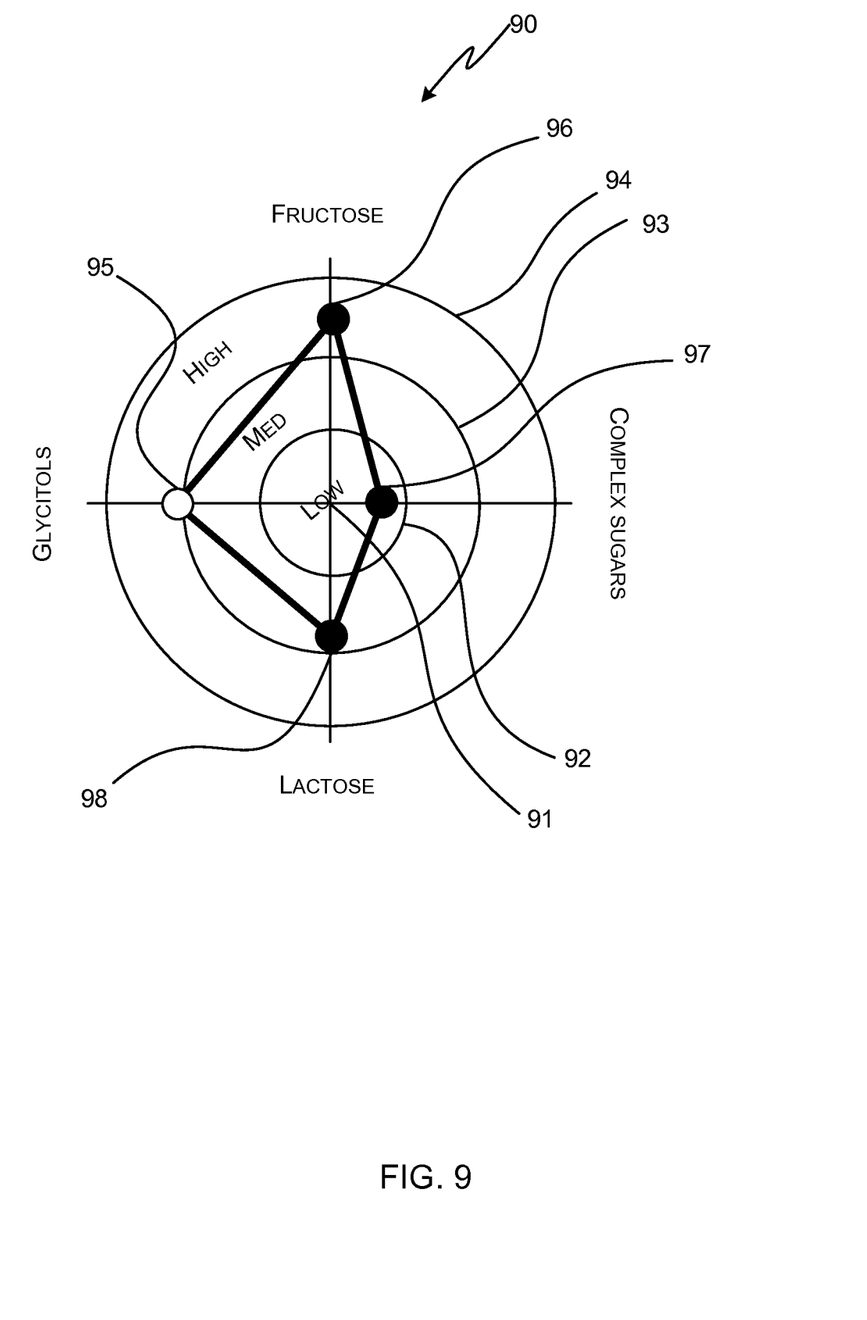
FIG. 9 shows another example of a user's digestive profile.

FIG. 9 shows another example of a chart 90 illustrating the user's digestive profile. Again, this graph may be generated from data stored in the storage module 29 of the user interface device 7.

The chart 90 comprises a polar graph with a centre point 91, a plurality of boundary lines 92, 93, 94 and four points 95, 96, 97, 98. Each point is associated with a descriptor of a food type.

The first point 95 is associated with 'glycitols' and its position on the graph indicates the user's suitability to 'glycitols'. Here, the first point 95 is positioned between the 'high' boundary line 94 and the 'med' boundary line 93. This indicates that the user's suitability to 'glycitols' is medium to high.

The second point 96 is associated with 'fructose'. The second point 96 is positioned between the 'high' boundary line 94 and the 'med' boundary line 93. This indicates that the user's suitability to 'fructose' is medium to high, but higher than for 'glycitols'.

The third point 97 is associated with 'complex sugars'. The third point 97 is positioned between the 'low' boundary line 92 and the centre point 91. This indicates that the user's suitability to 'complex sugars' is low.

The fourth point 98 is associated with 'lactose'. The fourth point 98 is positioned between the 'low' boundary line 92 and the 'med' boundary line 93. This indicates that the user's suitability to 'complex sugars' is medium to low.

In another example, the position of the points 95, 96, 97, 98 on the graph could indicate the user's gas readings in response to the relevant food type. For instance, the first point 95 may indicate that the user's gas readings in response to 'glycitols' are typically medium to high, and therefore 'glycitols' should be avoided.

The chart 90 provides a simple way of communicating the user's digestive profile whilst minimising the amount of space required for the chart 90 at the display of the interface device 7.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards etc and do not include propagated signals. The software can be suitable for execution on a parallel processor or a serial processor such that the method steps may be carried out in any suitable order, or simultaneously. This acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

It will be appreciated that the modules described herein may be implemented in hardware or in software. Furthermore, the modules may be implemented at various locations throughout the system, for instance at the breath analysis device 5, the user interface device 7 or the server 13. In addition, in some embodiments of the present disclosure the breath analysis device 5 and the user interface device 7 may be combined into a single unit.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person.

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method blocks or elements identified, but that such blocks or elements do not comprise an exclusive list and a method or apparatus may contain additional blocks or elements.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought. Any of the module described above may be implemented in hardware or software.

It will be understood that the above description of a preferred embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention.

The invention claimed is:

1. A digestive profiling system comprising:
   a remote user interface device comprising:
      a first communication interface arranged to receive a plurality of gas measurements generated by at least one gas sensor of a breath analysis device;
      a storage module arranged to store the received gas measurements; and
      a display arranged to display information to the user based on the stored gas measurements;
      a user interface module arranged to receive an input from a user identifying a food substance and an indication to associate the identified food substance with at least one of the plurality of gas measurements;
   wherein the association of the identified food substance with the gas measurement is indicative that the identified food substance was consumed by the user before providing the breath sample from which the associated gas measurement was generated; and wherein the system further comprises:
a profiling module arranged to generate a profile of the user by storing a plurality of different gas measurements each in association with their respective identified food substance; and
a ranking module arranged to determine a suitability score for each identified food substance based on the at least one of the plurality of gas measurements associated with each identified food substance;
wherein the remote user interface device is remote from the breath analysis device.

2. The digestive profiling system of claim 1 further comprising:
the breath analysis device comprising:
an inlet arranged to receive a breath sample from a user;
the at least one gas sensor arranged to generate a gas measurement of an amount of gas in the breath sample; and
a second communication interface arranged to transmit the plurality of gas measurements generated by the gas sensor.

3. The digestive profiling system according to claim 2, the system further comprising:
a plurality of the breath analysis devices; and
a server comprising:
a third communication interface arranged to receive gas measurements from the plurality of breath analysis devices; and
a storage module arranged to store the received gas measurements.

4. The digestive profiling system according to claim 3 wherein each of the received gas measurements is associated with at least one food substance; and
the server comprises:
an analysis module arranged to calculate an average suitability score for at least one of the food substances based on the received gas measurements.

5. The digestive profiling system according to claim 2 wherein the breath analysis device further comprises:
a temperature sensor arranged to generate a temperature measurement; and
a correction module arranged to adjust a gas measurement generated by the gas sensor based on the temperature measurement.

6. The digestive profiling system according to claim 2 where the breath analysis device further comprises:
a humidity sensor arranged to generate a humidity measurement; and
a correction module arranged to adjust a gas measurement generated by the gas sensor based on the humidity measurement.

7. The digestive profiling system according to claim 2 wherein the gas sensor is arranged to:
generate an ambient resistance value ($R_0$) in response to the ambient environment;
generate a sample resistance value ($R_{min}$) in response to a breath sample;
generate the gas measurement based on either the ratio of the sample resistance value ($R_{min}$) to the ambient resistance value ($R_0$) or
based on the ratio of the sample resistance value ($R_{min}$) to the ambient resistance value ($R_0$) and the difference between $R_0$ and $R_{min}$.

8. The digestive profiling system according to claim 1 wherein the ranking module determines the suitability score based on a negative correlation between the magnitude of the gas measurement and the suitability score.

9. The digestive profiling system according to claim 1 further comprising:
a storage module arranged to store a plurality of dietary information data items each stored in association with at least one food substance data item; and
a dietary module arranged to identify at least one food substance data item having a high suitability score, and identify at least one of the plurality of dietary information data items associated with the identified food substance data item;
wherein each dietary information data item is indicative of dietary information and each food substance data item is indicative of at least one food substance.

10. The digestive profiling system according to claim 1 wherein the user interface device further comprises:
output means arranged to prompt the user to provide a breath sample according to a predetermined schedule; and
a calibration module arranged to:
prompt the user, via output means, to consume a food substance sample;
prompt the user, via output means, to provide a breath sample at regular time intervals after prompting the user to consume the food substance sample;
identify a gut transit time based on a plurality of gas measurements generated in response to the user providing the breath samples; and
prompt the user, via output means, to provide a breath sample at regular time intervals up to a maximum time interval after prompting the user to consume the food substance sample;
wherein the regular time intervals are each approximately 15 minutes in duration; and
wherein the maximum time interval is approximately 3 hours in duration.

11. The digestive profiling system according to claim 10 further comprising a timer;
wherein the calibration module is arranged to activate the timer, in response to at least one of:
prompting the user to consume the food substance sample; and
receiving an indication that the user has consumed the food substance sample;
wherein prompting the user to provide a breath sample at regular time intervals is based on the timer.

12. The digestive profiling system according to any of claim 11 wherein the food substance sample comprises at least one of: lactulose, glucose, lactose, fructose, sorbitol, inulin, raffinose, xylitol, mannitol and/or any carbohydrate.

13. The digestive profiling system according to claim 1 further comprising:
a calibration module arranged to:
prompt the user, via output means, to consume a food substance sample;
after prompting the user to consume the food substance sample, prompt the user, via output means, to provide a breath sample after a predefined estimate of the user's gut transfer time; and
store a gas measurement generated by the gas sensor in response to the user providing the breath sample.

14. The digestive profiling system according to claim 1 further comprising a user interface module arranged to receive a food consumption indication from the user, indicating a start time of a food consumption session;

wherein the system further comprises a prompt module arranged to:
prompt the user, via output means, to provide a breath sample after a predefined estimate of the user's gut transfer time; and
store a gas measurement generated by the gas sensor, in response to the user providing the breath sample.

15. The digestive profiling system according to claim 1 wherein the remote user interface device is at least one of:
a smartphone;
a tablet; and
connected wirelessly to the breath analysis device via a wireless connection between the first communication interface and the second communication interface.

16. The digestive profiling system according to claim 1 wherein the gas sensor comprises a hydrogen and/or methane gas sensor arranged to generate a measurement of an amount of hydrogen and/or methane in the sample.

17. A method of generating a digestive profile for a user, the method comprising:
receiving a plurality of gas measurements, generated by at least one gas sensor at a breath analysis device, at a communication interface at a remote user interface device;
storing the received gas measurements at the remote user interface device; and
displaying the stored gas measurements at the remote user interface device;
receiving, at a user interface of the remote user interface device, an input from a user identifying a food substance and an indication to associate the identified food substance with at least one of the plurality of gas measurements, wherein the association of the identified food substance with the gas measurement is indicative that the identified food substance was consumed by the user before providing the breath sample from which the associated gas measurement was generated; and
generating, at a profiling module, a profile of the user by storing a plurality of different gas measurements each in association with their respective identified food substance; and
determining, at a ranking module, a suitability score for each identified food substance for the user based on the at least one of the plurality of gas measurements associated with each identified food substance.

18. A computer program comprising code portions which when loaded and run on a computer cause the computer to execute a method according to claim 17.

* * * * *